United States Patent
Mueller et al.

(10) Patent No.: US 9,279,029 B2
(45) Date of Patent: Mar. 8, 2016

(54) METHOD FOR PRODUCING LIGHT-COLOURED POLYISOCYANATES

(71) Applicant: Bayer Intellectual Property GmbH, Monheim (DE)

(72) Inventors: Thomas Ernst Mueller, Aachen (DE); Christoph Guertler, Köln (DE); Axel Scherer-Werke, Itzehoe (DE); Stefan Wershofen, Mönchengladbach (DE); Henning Vogt, Aachen (DE); Walter Leitner, Aachen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/352,865

(22) PCT Filed: Oct. 18, 2012

(86) PCT No.: PCT/EP2012/070613
§ 371 (c)(1),
(2) Date: Apr. 18, 2014

(87) PCT Pub. No.: WO2013/057165
PCT Pub. Date: Apr. 25, 2013

(65) Prior Publication Data
US 2014/0249289 A1    Sep. 4, 2014

(30) Foreign Application Priority Data
Oct. 21, 2011    (DE) .......................... 10 2011 084 965

(51) Int. Cl.
*C08G 18/76* (2006.01)
*C07C 263/10* (2006.01)

(52) U.S. Cl.
CPC .......... *C08G 18/7657* (2013.01); *C07C 263/10* (2013.01)

(58) Field of Classification Search
CPC ........................... C08G 18/7657; C07C 263/10
See application file for complete search history.

(56) References Cited

U.S. PATENT DOCUMENTS

| | | | |
|---|---|---|---|
| 3,459,781 A | 8/1969 | Hoeschele | |
| 4,465,639 A | 8/1984 | Hatfield | |
| 4,774,357 A | 9/1988 | Keggenhoff et al. | |
| 5,207,942 A | 5/1993 | Scherzer et al. | |
| 5,208,368 A | 5/1993 | Scherzer et al. | |
| 5,364,958 A | 11/1994 | Ishida et al. | |
| 5,872,278 A | 2/1999 | Kraus et al. | |
| 6,140,382 A | 10/2000 | Gallus et al. | |
| 6,576,788 B1 | 6/2003 | Penzel et al. | |
| 6,900,348 B1 | 5/2005 | Reif et al. | |
| 2007/0167646 A1 | 7/2007 | Wershofen et al. | |
| 2007/0179316 A1 | 8/2007 | Pohl et al. | |
| 2009/0240077 A1 | 9/2009 | Wershofen et al. | |
| 2011/0190535 A1* | 8/2011 | Carr et al. .................... | 560/358 |

FOREIGN PATENT DOCUMENTS

| | | |
|---|---|---|
| CA | 2038126 A1 | 9/1991 |
| DE | 19817691 A1 | 10/1999 |
| EP | 0133538 A2 | 2/1985 |
| EP | 0445602 A2 | 9/1991 |
| EP | 0446781 A1 | 9/1991 |
| EP | 0467125 A1 | 1/1992 |
| EP | 0538500 A1 | 4/1993 |
| EP | 0546398 A2 | 6/1993 |
| EP | 0561225 A2 | 9/1993 |
| EP | 0581100 A1 | 2/1994 |
| EP | 0866057 A2 | 9/1998 |
| EP | 1187808 A1 | 1/2001 |
| EP | 1808430 A1 | 7/2007 |
| EP | 1813598 A1 | 8/2007 |
| EP | 2103595 A1 | 9/2009 |

OTHER PUBLICATIONS

International Search Report for PCT/EP2012/070613 dated Mar. 3, 2013.

* cited by examiner

*Primary Examiner* — Michael L Leonard
(74) *Attorney, Agent, or Firm* — Drinker Biddle & Reath LLP

(57) ABSTRACT

The invention relates to a method for producing light-coloured polyisocyanates by phosgenation of mixtures comprising MDA and polycyclic aromatic polyamines that have o-phenylenediamine units incorporated via methylene bridges. The invention further relates to the polyisocyanate mixtures obtainable by this method.

10 Claims, No Drawings

METHOD FOR PRODUCING LIGHT-COLOURED POLYISOCYANATES

CROSS-REFERENCE TO RELATED APPLICATIONS

This application is a national stage application (under 35 U.S.C. §371) of PCT/EP2012/070613, filed Oct. 18, 2012, which claims benefit of German Application No. 10 2011 084 965.3, filed Oct. 21, 2011, both of which are incorporated herein by reference in their entirely.

The invention relates to a method for producing light-coloured polyisocyanates by phosgenation of mixtures comprising MDA and polycyclic aromatic polyamines that have o-phenylenediamine units incorporated via methylene bridges. The invention further relates to the polyisocyanate mixtures obtainable by this method.

Di- and polyamines of the diphenylmethane series (MDA) are understood to be amines and mixtures of amines corresponding to formula (I):

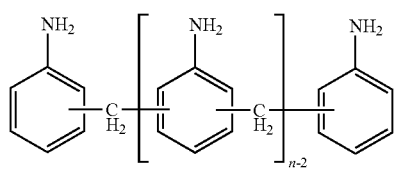

wherein n denotes a natural number ≥2.

For compounds and mixtures of compounds with n=2, the term monomeric MDA (MMDA) and for compounds and mixtures of compounds with n>2, the term polymeric MDA (PMDA) are also common. For the sake of simplicity, mixtures of compounds in which compounds with n=2 and n>2 occur together are generally referred to by the term MDA (di- and polyamines of the diphenylmethane series).

Isocyanates and isocyanate mixtures are produced according to the prior art by phosgenation of the appropriate amines. For polyurethane (PUR) foams, for example, di- or polyfunctional aromatic isocyanates of the diphenylmethane series (MDI) are used. As a result of the production process, after the phosgenation and subsequent work-up (separation of the solvent; separating of monomeric MDI) dark-coloured products are often obtained which in turn give discoloured polyurethane foams or other polyurethane materials that are also discoloured. This is undesirable, since this type of colouring adversely affects the overall visual impression and allows minor inhomogeneities to become more apparent, e.g. as streaks in the foams that are obtained. Light-coloured isocyanates, or isocyanates comprising a reduced quantity of colouring components, are therefore preferred as raw materials.

There has therefore been no lack of attempts to obtain isocyanates, and in particular di- and polyisocyanates of the diphenylmethane series (MDI), with a light colour. Numerous methods for the empirical colour lightening of MDI are known. The nature of the colouring substances that cause the problem (colouring molecules, colouring aggregates and/or colouring particles) is as yet insufficiently understood, however.

The known methods up to the present can be divided into five groups, which are presented below by way of examples with the aid of the citations listed:

1. Methods in which aniline with a specific degree of purity is used for the production of MDA.

EP-A1 1 813 598 teaches that the use of aniline comprising less than 3 wt. %, preferably 0.001 to 3 wt. %, particularly preferably 0.01 to 1 wt. % of di- and polyamines of the diphenylmethane series, based on the weight of the aniline used, in the production of MDA has an advantageous effect on the colour of the MDI produced therefrom by phosgenation. The di- and polyamines of the diphenylmethane series comprised in the aniline pass into the amine used for the production of MDA, since aniline is generally used in excess in MDA production and, after separation from the product e.g. by distillation, the excess is fed back into the process again.

Other secondary components comprised in aniline, such as e.g. cyclohexylamine, cyclohexanol, cyclohexanone, phenol etc., are listed e.g. in RD 510004 (Research Disclosure Journal, October 2006 publication) without any mention of the quantities in which these secondary components are comprised in the aniline or whether these secondary components have any influence on the quality of the MDA and of the MDI obtained therefrom.

EP-A1 2 103 595 describes a method for producing di- and polyamines of the diphenylmethane series (MDA) by reacting aniline and formaldehyde in the presence of an acidic catalyst, in which the aniline used comprises a total of less than 0.5 wt. %, preferably 0.0001 to 0.4 wt. %, particularly preferably 0.0001 to 0.3 wt. % and most particularly preferably 0.0001 to 0.25 wt. %, based on the weight of the aniline used, of compounds comprising at least one carbonyl group or which are formed by reaction of these compounds comprising at least one carbonyl group with aniline.

2. Methods in which the di- and polyamines of the diphenylmethane series (MDA) used as starting material have been subjected to a treatment and/or purification.

EP-A 0 546 398 describes a method for producing MDI, in which the MDA used as feedstock is acidified before the phosgenation.

EP-A 0 446 781 relates to a method for producing MDI, in which the MDA is first treated with hydrogen and then subjected to phosgenation, wherein a lighter-coloured MDI is obtained.

The aforementioned methods give only a slight improvement in colour, since experience has shown that the colouring substances in the MDI consist not only of certain secondary components of MDA production, but also result from colour precursors which are formed by secondary reactions during phosgenation.

3. Process engineering solutions in the phosgenation process

U.S. Pat. No. 5,364,958 relates to a method for producing isocyanates, in which the phosgene is removed completely at low temperature after phosgenation and then the isocyanate is treated with HCl gas at a high temperature.

In DE-A-1981 7691, a method is described for producing MDI with a reduced content of chlorinated by-products and reduced iodine colour value by adherence to defined parameters in the phosgenation reaction. In particular here, adherence to specific phosgene/HCl ratios in the reaction step is necessary. This method has the disadvantage that it is more difficult to vary the parameters in the phosgenation and, as a result, the quality of the phosgenation becomes very sensitive. The lack of flexibility in the phosgenation parameters also makes practical implementation of the phosgenation very difficult and requires complex technical measures.

Another possible way of improving the colour of isocyanates is, according to EP-B 1 187 808, the use of phosgene with low bromine and/or iodine contents.

EP-B 1 808 430 describes an improvement in the colour of isocyanates through the use of phosgene having only a low content of sulfur in elemental or bound form in the phosgenation.

Although methods of the aforementioned type attempt to separate off the components causing discolorations at the correct point, however, they are too inefficient both because of their high technical complexity and in terms of their colour-lightening effect, since there is only slight degradation of colour precursors that are formed by incomplete chemical reactions.

4. Addition of colour-lightening additives to the crude isocyanate product on completion of phosgenation and before the work-up, e.g. by distillation.

EP-A 0 581 100 relates to a method for producing isocyanates in which, after phosgenation, a chemical reducing agent is added before the solvent is separated off, light-coloured products likewise being obtained according to this document.

According to U.S. Pat. No. 4,465,639, water is added to the crude product obtained after phosgenation to lighten the colour. For the same purpose, EP-A 538 500, EP-A 0 445 602 and EP-A 0 467 125 describe the addition of carboxylic acids, alkanols and polyether polyols respectively.

Although the colour-lightening methods described above are efficient, they do however have disadvantages in that, in addition to colour lightening, the additives that are added enter into reactions with the isocyanates that are obtained as the product, resulting for example in an undesirable reduction of the isocyanate content. There is also the risk of the formation of undesirable by-products in the MDI.

5. Post-treatment of the end product

EP-A 0 133 538 describes the purification of isocyanates by extraction, as a result of which fractions of a light-coloured MDI are obtained.

EP-A 0 561 225 relates to a method for producing isocyanates or isocyanate mixtures which, according to this document, have no colouring components, wherein after phosgenation of the corresponding amine, the isocyanates are subjected to a hydrogen treatment under a pressure of 1 to 150 bar and at a temperature of 100 to 180° C. According to the examples described there, isocyanate end products are hydrogenated as such or in the form of solutions thereof in suitable solvents.

These colour-improving post treatments of the isocyanate end products after the complete separation of the solvent at elevated temperature are also not very efficient, since as a result of the high temperatures that occur in the work-up, in particular the distillation of the solvent and optionally of monomeric MDI (diisocyanates), stable colouring substances have already formed, the chemical degradation of which can be achieved only with difficulty.

The object of the present invention consisted in providing a simple and economical method for producing light-coloured polyisocyanates. The method should be accomplished without the aforementioned treatment steps and yet lead to light-coloured isocyanates which are suitable for the production of polyurethanes or precursors thereof (e.g. prepolymers).

Surprisingly, it has been found that, by phosgenation of mixtures comprising MDA and polycyclic aromatic polyamines that have o-phenylenediamine units incorporated via methylene bridges, polyisocyanate mixtures are obtained which, compared with polyisocyanates based on MDI alone, have a significantly reduced grey value with approximately the same yellowness index.

The invention therefore provides a method for producing light-coloured polyisocyanate mixtures by phosgenation of mixtures comprising MDA and polycyclic aromatic polyamines of formula (II) and/or (III)

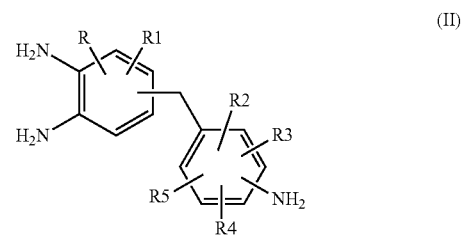

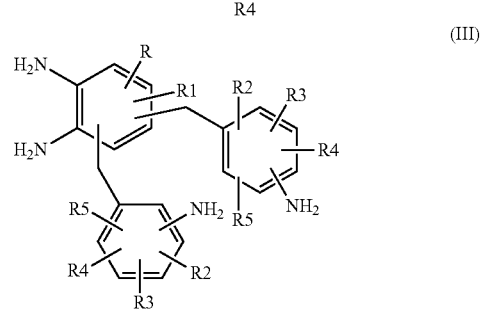

and/or higher homologs of the compounds of formula (II) and/or (III), wherein

R denotes hydrogen, an optionally substituted or heteroatom-comprising, saturated or unsaturated alkyl, cycloalkyl, aralkyl or aryl residue and R1 denotes hydrogen, an optionally substituted or heteroatom-comprising, saturated or unsaturated alkyl, cycloalkyl, aralkyl or aryl residue, or R and R1 are directly linked to one another so that they form a bicyclic structural element together with the phenylenediamine partial structure, and R2, R3, R4 and R5 independently of one another denote hydrogen or an optionally substituted or heteroatom-comprising, saturated or unsaturated alkyl, cycloalkyl, aralkyl or aryl residue in ortho, meta or para position to the amino group that is bound to the same aromatic ring.

Some or all of the residues R2, R3, R4 and R5 can also be directly linked to one another so that they form bi-, tri- or tetracyclic systems together with the aromatic system that is bound to the amino group.

R and R1 independently of one another denote (a) hydrogen, (b) a saturated or unsaturated alkyl residue, such as e.g. methyl, ethyl, vinyl, propyl, allyl, isopropyl, the various isomeric butyl residues, the various isomeric pentyl residues, the various isomeric hexyl residues, linear or branched alkyl residues with more than 6 C atoms, (c) a saturated or unsaturated cycloalkyl residue, such as e.g. cyclopropyl, cyclobutyl, cyclopentyl, cyclopentenyl, cyclopentadienyl, cyclohexyl, (d) a saturated or unsaturated aralkyl residue, such as e.g. benzyl, 2-phenylvinyl or (e) an aryl residue, such as e.g. phenyl. The said residues R and R1 may optionally also carry further substituents and optionally comprise atoms other than carbon and hydrogen (heteroatoms), such as e.g. oxygen, nitrogen, fluorine, chlorine, bromine R and R1, independently of one another, preferably denote hydrogen or methyl.

The residues R2 to R5 are preferably hydrogen.

The residue $(H_2N)_2C_6HRR1$ in formula (II) or $(H_2N)_2C_6RR1$ in formula (III) is particularly preferably derived from o-phenylenediamine, 1,2-diamino-3-methylbenzene (2,3-TDA) or 1,2-diamino-4-methylbenzene (3,4-TDA), most particularly preferably from 1,2-diamino-3-methylbenzene or 1,2-diamino-4-methylbenzene.

Mixtures comprising various compounds of formula (II) and/or (III) and/or the higher homologs of formula (II) and/or (III), which differ in the nature and position of the residues R, R1, R2, R3, R4 and R5, can also be used.

Higher homologs within the meaning of the invention refer to compounds in which any number of compounds of formula (IV), also designated generally below as o-phenylenediamines,

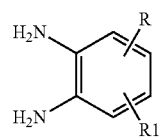
(IV)

and/or of formula (V)

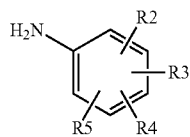
(V)

wherein R and R1 to R5 have the meaning given above, are linked to one or more of the aromatic carbon atoms via methylene groups to form linear or branched chains or cyclic structures, wherein at least one o-phenylenediamine (compound of formula (IV)) is comprised in the molecule.

The content of polycyclic aromatic polyamines (II) and (III) and/or higher homologs thereof in the starting mixtures is 0.001 to 5, preferably 0.001 to 3.5, particularly preferably 0.001 to 2 wt. %, based on the total weight of MDA, the polycyclic aromatic polyamines (II) and (III) and higher homologs thereof.

In particular, the content of the polycyclic aromatic polyamines (II) and (III) in the starting mixtures is 0.001 to 2, preferably 0.001 to 1, particularly preferably 0.001 to 0.5 wt. %, based on the total weight of MDA, the polycyclic aromatic polyamines (II) and (III) and higher homologs thereof. The precise definition of the indication "wt. %" can be taken from the description of the analytical method in the experimental part below.

The invention further provides polyisocyanate mixtures obtainable by the method according to the invention.

The invention further provides polyisocyanate mixtures comprising MDI and polycyclic aromatic polyisocyanates that are derived from the aforementioned polycyclic aromatic polyamines (II) and/or (III) and higher homologs thereof, wherein R and R1 to R5 have the meaning given above.

Derived, within the meaning of the invention, means that the amino groups of the polyamines (II) or (III) or higher homologs thereof are replaced completely or in part by isocyanate groups.

In the phosgenation of the polyamines (II) or (III) or higher homologs thereof, the o-phenylenediamine units that are comprised can also be converted to the corresponding cyclic ureas.

The content of these polycyclic aromatic polyisocyanates that are derived from the aforementioned polycyclic aromatic polyamines (II) and (III) and higher homologs thereof in the claimed polyisocyanate mixtures is 0.001 to 5, preferably 0.001 to 3.5, particularly preferably 0.001 to 2 wt. %, based on the total weight of MDI and the polycyclic aromatic polyisocyanates that are derived from the aforementioned polycyclic aromatic polyamines (II) and (III) and higher homologs thereof.

In particular, the content of the polycyclic aromatic polyisocyanates that are derived from the aforementioned polycyclic aromatic polyamines (II) and (III) in the starting mixtures is 0.001 to 2, preferably 0.001 to 1, particularly preferably 0.001 to 0.5 wt. %, based on the total weight of MDI and the polycyclic aromatic polyisocyanates that are derived from the polycyclic aromatic polyamines (II) and (III) and higher homologs thereof.

The MDA/polyamine mixtures to be used in the method according to the invention are obtainable e.g. by co-condensation of o-phenylenediamines (formula IV) and aniline or of a mixture comprising aniline and one or more primary aromatic monoamines of formula V, in which at least one carbon atom located in ortho or para position to the amino group carries a hydrogen substituent, with formaldehyde, wherein the quantity of o-phenylenediamines used is 0.001 to 2, preferably 0.001 to 1.5, particularly preferably 0.001 to 0.9 wt. %, based on the weight of the aniline used and the monoamines used.

The co-condensation in this case can be performed in such a way that aniline or the mixture comprising aniline and one or more primary aromatic monoamines of formula V and formaldehyde are pre-condensed with protonic acid catalysts to form intermediates and then the o-phenylenediamines are added either to the reaction mixture or to isolated intermediates.

Formaldehyde is generally used industrially as an aqueous solution, which is present in concentrations of 30-50 wt. %. However, it is also possible to use aqueous formaldehyde solutions of a different concentration, gaseous formaldehyde, solutions of formaldehyde in a solvent other than water or other compounds providing methylene groups, such as e.g. polyoxymethylene glycol, paraformaldehyde or trioxane. The aqueous formaldehyde solutions can also comprise methanol, generally in the concentration range of 0.001-15 wt. %, based on the aqueous formaldehyde solution, and/or formic acid, generally in the concentration range of 0.0001-0.1 wt. %, preferably 0.0001-0.03 wt. %, based on the aqueous formaldehyde solution.

Protonic acids are any protonic acid with a $pK_a$ value of less than 3, for example hydrochloric acid, (aqueous) HBr, (aqueous) HI, sulfuric acid, p-toluenesulfonic acid, methanesulfonic acid, phosphoric acid, perchloric acid, trichloroacetic acid, trifluoroacetic acid, trifluoromethanesulfonic acid, acidic ion exchangers with sulfonic acid groups and solid acid such as aluminosilicates, zeolites or mesoporous aluminosilicates. A preferred acid is hydrochloric acid.

No additional solvent is generally used for the reaction; excess aniline or excess mixture comprising aniline and one or more primary aromatic monoamines of formula V acts as solvent. It is possible, however, to carry out the reaction in the presence of an additional solvent or mixtures of several additional solvents. Suitable solvents are e.g. water, alcohols, such as methanol, ethanol, the isomeric propanols, the isomeric butanols, higher alcohols, chlorobenzene, dichlorobenzene, dimethylformamide, dimethylacetamide, dimethyl sulfoxide, N-methylpyrrolidone, 1,4-dioxane, tetrahydrofuran, glycol and higher homologs thereof $H(O-CH_2-CH_2-)_nOH$ ($n \geq 2$).

Aniline or a mixture comprising aniline and one or more primary aromatic monoamines of formula V and formaldehyde are used in a molar ratio of 1.5:1 to 10:1, preferably 1.5:1 to 6:1, particularly preferably 1.8:1 to 4:1 and most particularly preferably 1.8:1 to 2.5:1. The molar ratio of the protonic acid, preferably hydrochloric acid, to the aniline or to the mixture comprising aniline and one or more primary aromatic monoamines of formula V is generally 1:100 to 1:1, preferably 1:100 to 1:2, particularly preferably 1:50 to 1:5 and most particularly preferably 1:20 to 1:10.

The method can be carried out e.g. in such a way that aniline or the mixture comprising aniline and one or more primary aromatic monoamines of formula V, formaldehyde solution and hydrochloric acid are placed in a stirred vessel and mixed and optionally, parallel to the reaction that is taking place, part of the water is removed by distillative separation. Aniline or the mixture comprising aniline and one or more primary aromatic monoamines of formula V, the formaldehyde solution and hydrochloric acid may optionally also be added in a batchwise method via time-based metering profiles, wherein the water separation can take place during or after the addition of the feedstocks, for example by vacuum distillation. The mixing of aniline or the mixture comprising aniline and one or more primary aromatic monoamines of formula V, formaldehyde solution and aqueous HCl takes place at temperatures of 0 to 80° C., preferably 20 to 60° C. and particularly preferably 30 to 40° C.

The method can also be carried out in such a way that aniline or the mixture comprising aniline and one or more primary aromatic monoamines of formula V and formaldehyde are mixed and reacted in the absence of the acidic catalyst at temperatures of 20° C. to 100° C., preferably of 40° C. to 100° C., particularly preferably of 60° C. to 95° C. In this case, condensation products of aniline or aniline and the primary aromatic monoamines of formula V used and formaldehyde (so-called aminal) are formed. Following the formation of aminal, the water comprised in the aminal is at least partly removed, for example by phase separation or by other suitable methods, for example by distillation. The addition of the acidic catalyst and the removal of the water can take place e.g. in such a way that, in a stirred vessel containing the aminal that has been produced, aqueous HCl is added and optionally part of the water is removed by distillative separation during the reaction to form the condensation product.

In a particular variant of this embodiment, aniline or the mixture comprising aniline and one or more primary aromatic monoamines of formula V and formaldehyde are initially mixed and reacted in the absence of the acidic catalyst at temperatures of 20° C. to 100° C., preferably of 40° C. to 100° C., particularly preferably of 60° C. to 95° C. During this process, condensation products of aniline or aniline and the primary aromatic monoamines of formula V that are used and formaldehyde are formed (so-called aminal). Following the formation of the aminal, the water comprised in the aminal is at least partially removed, for example by phase separation or by other suitable methods, for example by distillation. The aminal is then mixed with hydrochloric acid at temperatures of 0 to 80° C., preferably 20 to 60° C. and particularly preferably 30 to 40° C.

The o-phenylenediamine of formula (IV) or a mixture of two or more o-phenylenediamines of the general formula (IV), wherein the constituents of the said mixture may be present in any quantitative ratios, is fed into the reaction mixture obtained in accordance with one of the above embodiments at temperatures of 0 to 100° C., preferably 20 to 80° C. and particularly preferably 60 to 80° C.

The o-phenylenediamine or a mixture of two or more o-phenylenediamines is added as the substance itself (as a solid or liquid or melt) or as a solution in a suitable solvent. Suitable solvents are e.g. water, alcohols, such as methanol, ethanol, the isomeric propanols, the isomeric butanols, higher alcohols, chlorobenzene, dichlorobenzene, dimethylformamide, dimethylacetamide, dimethyl sulfoxide, N-methylpyrrolidone, 1,4-dioxane, tetrahydrofuran, glycol and higher homologs thereof $H(O-CH_2-CH_2-)_nOH$ ($n \geq 2$), primary aromatic monoamines of formula (V), such as e.g. aniline, or mixtures thereof.

Based on 1 mol aniline or 1 mol of the mixture comprising aniline and one or more primary monoamines of formula (V), generally 0.000 01-0.02 mol of the o-phenylenediamine of formula (IV) or of a mixture consisting of two or more o-phenylenediamines of formula (IV), preferably 0.000 01-0.015 mol, particularly preferably 0.000 01-0.009 mol, are used.

The point at which the o-phenylenediamine of formula (IV) or a mixture consisting of two or more o-phenylenediamines of the general formula (IV) is added is selected so that the formaldehyde is virtually completely reacted and the methylene groups that are formed are substituted by fewer than two heteroatoms. As a result, the formation of secondary components with a benzimidazole structure is largely avoided.

Depending on the other process parameters, therefore, the o-phenylenediamine of formula (IV) or a mixture consisting of two or more o-phenylenediamines of the general formula (IV) is generally added as the substance itself or in solution 0.01-200 min, preferably 0.1-200 min, particularly preferably 20-120 min after mixing the primary amine of formula (V), the formaldehyde (solution) and the protonic acid.

The temperature of the reaction mixture is preferably brought, in steps or continuously and optionally under excess pressure, to a temperature of 110° C. to 250° C., particularly preferably of 110° C. to 180° C., most particularly preferably of 110° C. to 160° C. The residence time is preferably selected so that intermediates with an aminobenzylaniline structure are completely reacted.

To work up the acidic reaction mixture, the reaction mixture is generally neutralised with a base. According to the prior art, the neutralisation generally takes place at temperatures of for example 90 to 100° C. without adding any other substances (H. J. Twitchett, Chem. Soc. Rev. 3(2), 223 (1974)). However, it can also take place at another temperature level, e.g. in order to accelerate the degradation of unwanted by-products. Suitable as bases are, for example, the hydroxides of the alkali and alkaline earth elements. Aqueous NaOH solution is preferably used.

The base used for neutralisation is preferably used in quantities of more than 100%, particularly preferably 105 to 120%, of the stoichiometric quantity needed to neutralise the acidic catalyst used.

Following neutralisation, the organic phase is generally separated from the aqueous phase in a separating vessel. The product-comprising organic phase that remains after separating off the aqueous phase is then generally subjected to further work-up steps (e.g. washing with water) and then freed from excess aniline and other substances present in the mixture (e.g. other solvents) by suitable methods, such as e.g. distillation, extraction or crystallisation.

According to the method of the invention, mixtures comprising MDA and polycyclic aromatic polyamines of formula (II) and/or (III) and/or higher homologs thereof are reacted with phosgene in an inert organic solvent to form the corresponding polyisocyanate mixtures. The ratio of the mixture used comprising MDA and polycyclic aromatic polyamines of formula (II) and/or (III) and/or higher homologs thereof to phosgene is usefully calculated so that, per mol of $NH_2$ group, 1 to 10 mol, preferably 1.3 to 4 mol, phosgene are present in the reaction mixture.

Any solvents that are suitable for the production of isocyanates can be used as solvent. These are preferably inert aromatic, aliphatic or alicyclic hydrocarbons or halogenated derivatives thereof. Examples of such solvents are aromatic compounds, such as monochlorobenzene, dichlorobenzene, for example o-dichlorobenzene, trichlorobenzene, toluene, xylenes, naphthalene derivatives, such as tetralin or decalin, alkanes with about 5 to about 12 C atoms, such as hexane, heptane, octane, nonane or decane, cycloalkanes, such as cyclohexane, inert esters and inert ethers, such as ethyl acetate or butyl acetate, tetrahydrofuran, dioxane or diphenyl ether. In particular, monochlorobenzene, dichlorobenzene or mixtures of these chlorobenzenes are used as inert organic solvents. The quantity of solvent is usefully calculated so that the resulting reaction mixture has a content of aromatic (poly) isocyanates of 2 to 50 wt. %, preferably between 5 and 30 wt. %, based on the total weight of the reaction mixture.

In an alternative embodiment, the reaction with phosgene is performed in the absence of a solvent.

The phosgenation can take place continuously or batchwise in one or more steps. If a one-step reaction is performed, this reaction takes place for example at about 60 to 200° C., preferably at about 130 to 180° C.

In another embodiment of the invention, the reaction can be performed in two steps. In this case, in a first step the reaction of the phosgene with the mixture comprising MDA and polycyclic aromatic polyamines of formula (II) and/or (III) and/or higher homologs thereof is preferably performed at a temperature of 0 to 140° C., particularly preferably 20 to 120° C., most particularly preferably 40 to 110° C., a period of 1 min to 2 h preferably being allowed for the reaction between amine and phosgene. In a second step, during a period of 1 min to 5 h, preferably of 1 min to 3 h, the temperature is then increased to 60 to 200° C., preferably 70 to 170° C.

In a preferred embodiment of the invention, the reaction is performed in two steps.

During the reaction, an increased absolute pressure of 100 bar or less, preferably 1 bar to 50 bar, particularly preferably 2 bar to 40 bar, most particularly preferably 3 bar to 25 bar, can be applied.

However, the reaction can also take place without pressure. In another embodiment of the invention, therefore, work is carried out at atmospheric pressure, i.e. generally at about 1 bar absolute pressure. In another embodiment, it is also possible to work at reduced pressure compared with atmospheric pressure.

On completion of phosgenation, the excess phosgene and the inert organic solvent or mixtures thereof are separated off from the reaction mixture by distillation according to the prior art. The removal of the excess phosgene preferably takes place at a temperature of 50 to 200° C. The removal of the residual traces of solvent preferably takes place under reduced pressure. The absolute pressure is preferably 500 mbar or less, particularly preferably less than 100 mbar. In general, the various components are separated off in the order of their boiling points; it is also possible to separate off mixtures of the various components in a single process step.

From the crude isocyanate obtained, product mixtures comprising bicyclic and polycyclic mono-, di- and polyisocyanates as well as products comprising bicyclic mono-, di- and/or triisocyanates or mixtures thereof can be produced in the same way as in the prior art known for MDI. The separation of these products from the crude MDI can take place according to the prior art, for example by distillation or crystallisation. These products are suitable for use as light-coloured raw materials for polyurethane production in the form of polymers and prepolymers by reaction with polyols.

The following examples illustrate the present invention.

EXAMPLES

GWP 1: General working procedure for preparing mixtures comprising MDA and optionally polycyclic aromatic polyamines that have o-phenylenediamine units incorporated via methylene bridges:

In a double-walled flask with a mechanical stirrer, which has been preheated to 80° C., 300 g (3.22 mol) aniline are initially charged and heated to 80° C. with the exclusion of air. Within 20 min, 631.3 g (6.78 mol) aniline and 401.5 g (3.75 mol) of a 37.4% aqueous formaldehyde solution are added simultaneously. After the reaction mixture has been stirred for a further 10 min at 80° C., the two resulting phases are separated. Approx. 300 g of the organic phase ("aminal") are preheated to 35° C. in a flask with stirring and with the exclusion of air. Then, within 30 min at 35° C., the residual "aminal" and 112.7 g (1 mol) of 32.4% hydrochloric acid are simultaneously added dropwise. The exothermic heat generated is taken up by external cooling. The mixture is then stirred for a further 90 min at 35° C. The reaction mixture is then heated to 80° C. within 10 min, a 60% solution of o-TDA (mixture of isomers consisting of approx. 60% 3,4-TDA and 40% 2,3-TDA) in water preheated to 70° C. is added (for quantitative data, see Table 1) and the resulting reaction mixture is stirred for a further 30 min at 80° C. before the temperature is raised to reflux (approx. 105° C.) within 30 min. The reaction mixture is stirred at this temperature for a further 15 h. The reaction mixture is alkalised by adding 150 g (1.125 mol) 30% aqueous sodium hydroxide solution and 400 ml distilled water. After continuing to stir for 15 min at approx. 100° C. and phase separation, the organic phase is washed twice at approx. 100° C. with 400 ml boiling distilled water. The organic phase that is obtained is finally removed by means of distillation of water and excess aniline in an oil pump vacuum. The product remains as bottoms in the bottom flask of the distillation.

The analysis of the reaction product took place by HPLC:

Instrument: Agilent 1100 Series HPLC System

Column: Spherisorb ODS2/3 μm/75×4.6 mm/MZ-Analysentechnik item no. 75.4,6.7063.N Temperature: 35° C.

Injection volume: 5 μl

DAD signal: 240 nm Bw 12 nm/reference 550 nm Bw 40 nm

Eluent A: acetonitrile (Chromasolv/Sigma Aldrich/34851-2.5 1)

Eluent B: demineralised water with 1.9 g ammonium acetate per litre (HPLC grade/Sigma Aldrich/17836-50 g)

Eluent C: methanol (gradient/Sigma Aldrich/m.1.06007.2500)

Gradient:

| Time [min] | CH$_3$CN [%] | Water [%] | Methanol [%] | Flow [ml/min] |
|---|---|---|---|---|
| 0.00 | 6.0 | 74.0 | 20.0 | 1.60 |
| 1.00 | 6.0 | 74.0 | 20.0 | 1.60 |
| 2.00 | 8.0 | 72.0 | 20.0 | 1.60 |
| 2.50 | 8.0 | 72.0 | 20.0 | 1.60 |
| 4.50 | 15.0 | 65.0 | 20.0 | 1.60 |
| 7.50 | 15.0 | 65.0 | 20.0 | 1.60 |
| 8.00 | 20.0 | 60.0 | 20.0 | 1.60 |
| 14.00 | 26.0 | 54.0 | 20.0 | 1.60 |
| 15.00 | 32.0 | 48.0 | 20.0 | 1.60 |
| 21.00 | 32.0 | 48.0 | 20.0 | 1.60 |
| 22.00 | 40.0 | 40.0 | 20.0 | 1.60 |
| 23.00 | 45.0 | 35.0 | 20.0 | 1.60 |
| 24.00 | 55.0 | 25.0 | 20.0 | 1.60 |
| 25.00 | 60.0 | 20.0 | 20.0 | 1.60 |
| 27.00 | 60.0 | 20.0 | 20.0 | 1.60 |
| 27.50 | 32.0 | 48.0 | 20.0 | 1.60 |
| 28.00 | 6.0 | 74.0 | 20.0 | 1.60 |
| 30.00 | 6.0 | 74.0 | 20.0 | 1.60 |

Calibration: for 4,4'-MDA, 2,4'-MDA and 2,2'-MDA, a multi-point calibration was performed with pure substances. Since no suitable pure substances were available for the polycyclic aromatic polyamines (II) and (III), the response factor for 4,4'-MDA was used for quantifying these compounds owing to the structural similarity. The statement of content in wt. % is therefore based on the use of the response factor for 4,4'-MDA for these compounds. The allocation of the corresponding signals for the polycyclic aromatic polyamines (II) and (III) took place by HPLC-MS.

Sample preparation: approx. 50-60 mg of sample are weighed into a 50 ml measuring flask. The measuring flask is topped up with acetonitrile to the 50 ml calibration mark. Part of this solution is transferred into an HPLC septum bottle and used for the analysis.

GWP 2: General working procedure for the phosgenation:
Starting materials:
amine mixture, comprising MDA and optionally polycyclic aromatic polyamines that have o-phenylenediamine units incorporated via methylene bridges, obtained by acid catalysed condensation of aniline and optionally o-TDA with formaldehyde according to the general working procedure GWP 1. For the content of components of formula (II) and (III), see Table 1.
chlorobenzene, anhydrous
phosgene 15 g of the amine mixture are dissolved in 70 ml chlorobenzene, heated to 55° C. and added within 10 s with vigorous stirring to a solution of 32 g phosgene in 80 ml chlorobenzene cooled to 0° C. While passing phosgene through the suspension, this is heated to 100° C. within 45 min and then heated to reflux temperature for 10 min After a further 10 min at this temperature, the solvent is distilled off under reduced pressure to a bottom temperature of 100° C. The crude isocyanate is then heated in a distillation apparatus under a pressure of 4 to 6 mbar by means of a hot air blower until the first product transition takes place and then cooled to ambient temperature with cold air within 5 to 10 min Of the isocyanate thus obtained, 1.0 g is dissolved in chlorobenzene and diluted to 50 ml with chlorobenzene. The absorbance of the solution thus obtained is determined at the two wavelengths of 430 nm and 520 nm. A Dr. Lange LICO 300 photometer is used as the measuring instrument.

Comparative Example

Phosgenation of MDA according to GWP 2. The amine mixture was obtained according to GWP 1 by acid-catalysed condensation of aniline with formaldehyde and comprised no components of formula (II) or (III). The results of the characterisation of the amine mixture used and the polyisocyanate mixtures obtained are compiled in Table 1.

Example 1

Phosgenation of an amine mixture comprising MDA and polycyclic aromatic polyamines that have o-phenylenediamine units incorporated via methylene bridges according to GWP 2. The amine mixture was obtained according to GWP 1 by acid-catalysed condensation of aniline with formaldehyde and 4.7 g (0.039 mol; 0.5 wt. % based on aniline) The amine mixture comprised 0.02 wt. % components of formula (II) and 0.13 wt. % components of formula (III). The results of the characterisation of the amine used and the polyisocyanate mixtures obtained are compiled in Table 1.

Example 2

Phosgenation of an amine mixture comprising MDA and polycyclic aromatic polyamines that have o-phenylenediamine units incorporated via methylene bridges according to GWP 2. The amine mixture was obtained according to GWP 1 by acid-catalysed condensation of aniline with formaldehyde and 9.3 g (0.076 mol; 1.0 wt. % based on aniline) The amine mixture comprised 0.23 wt. % components of formula (II) and 0.30 wt. % components of formula (III). The results of the characterisation of the amine used and the polyisocyanate mixtures obtained are compiled in Table 1.

TABLE 1

|  |  | Comparative example | Example 1 | Example 2 |
|---|---|---|---|---|
| o-TDA | [g] | 0 | 4.7 | 9.3 |
|  | [mol] | 0 | 0.039 | 0.076 |
| o-TDA based on aniline | [wt. %] | 0 | 0.5 | 1 |
|  | [mole %] | 0 | 0.5 | 0.9 |
| Reaction of aniline/o-TDA with formaldehyde: |  |  |  |  |
| 4,4'-MDA | [wt. %] | 50.97 | 52.03 | 50.96 |
| 2,4'-MDA | [wt. %] | 4.42 | 4.47 | 4.42 |
| 2,2'-MDA | [wt. %] | 0.16 | 0.17 | 0.22 |
| Total bicyclic MDA | [wt. %] | 56.2 | 57.0 | 55.9 |
| Component (II) | [wt. %] | 0 | 0.02 | 0.23 |
| Component (III) | [wt. %] | 0 | 0.13 | 0.30 |
| Phosgenation: |  |  |  |  |
| E430 |  | 0.111 | 0.127 | 0.130 |
| E520 |  | 0.029 | 0.010 | 0.007 |
| E430/E520 |  | 4 | 13 | 19 |
| Viscosity | [mPas] | 89 | 77 | 94 |
| NCO | [wt. %] | 32.52 | 32.61 | 32.23 |

Examples 1 and 2 illustrate that, compared with the comparative example, when using a mixture comprising MDA and polycyclic aromatic polyamines of formula (II) and/or (III), and/or higher homologs thereof, obtained by addition of o-TDA to the reaction of aniline and formaldehyde, the isocyanate obtained after phosgenation has a significantly lower grey value (E520) with approximately the same yellowness index (E430). Associated with this is also a significant increase in the ratio of yellowness index to grey value (E430/E520). Thus, the advantageous effect of o-phenylenediamine structures on the colour of the isocyanate obtained is demonstrated.

The invention claimed is:

1. A method for producing light-coloured polyisocyanate mixtures by phosgenation of mixtures comprising MDA and polycyclic aromatic polyamines of formula (II) and/or (III)

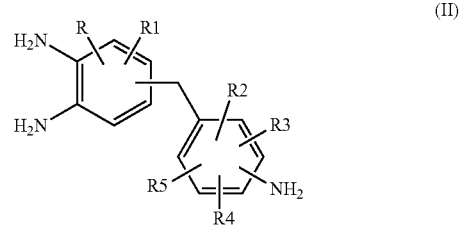

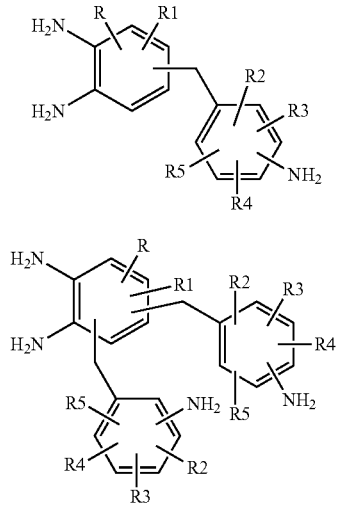

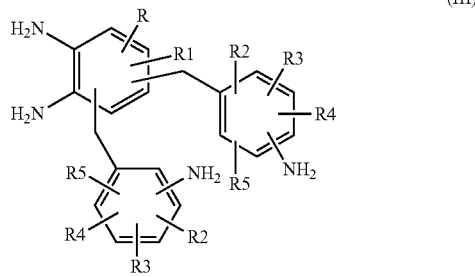

and/or higher homologs of the compounds of formula (II) and/or (III), wherein

R denotes hydrogen, an optionally substituted or heteroatom-comprising, saturated or unsaturated alkyl, cycloalkyl, aralkyl or aryl residue and R1 denotes hydrogen, an optionally substituted or heteroatom-comprising, saturated or unsaturated alkyl, cycloalkyl, aralkyl or aryl residue, or R and R1 are directly linked to one another so that they form a bicyclic structural element together with the phenylenediamine partial structure, and R2, R3, R4 and R5 independently of one another denote hydrogen or an optionally substituted or heteroatom-comprising, saturated or unsaturated alkyl, cycloalkyl, aralkyl or aryl residue in ortho, meta or para position to the amino group that is bound to the same aromatic system, and wherein the content of the polycyclic aromatic polyamines (II) and (III) and/or higher homologs thereof in the starting mixtures is 0.001 to 5 wt. %, based on the total weight of MDA, the polycyclic aromatic polyamines (II) and (III) and higher homologs thereof.

2. The method according to claim 1, wherein R and R1 independently of one another denote hydrogen or methyl and/or the residues R2 to R5 denote hydrogen.

3. The method according to claim 1, wherein the residue $(H_2N)_2C_6HRR1$ in formula (II) or $(H_2N)_2C_6RR1$ in forumula (III) is derived from o-phenylenediamine, 1,2-diamino-3-methylbenzene or 1,2-diamino-4-methylbenzene.

4. The method according to claim 1, wherein the content of the polycyclic aromatic polyamines (II) and (III) in the starting mixtures is 0.001 to 2 wt. %, based on the total weight of MDA, the polycyclic aromatic polyamines (II) and (III) and higher homologs thereof.

5. Polyisocyanate mixtures obtainable by a method according to claim 1.

6. Polyisocyanate mixtures comprising MDI and polycyclic aromatic polyisocyanates that are derived from MDA and the polycyclic aromatic polyamines of formulae (II) and (III) and/or higher homologs thereof, wherein R denotes hydrogen, an optionally substituted or heteroatom-comprising, saturated or unsaturated alkyl, cycloalkyl, aralkyl or aryl residue and R1 denotes hydrogen, an optionally substituted or heteroatom-comprising, saturated or unsaturated alkyl, cycloalkyl, aralkyl or aryl residue, or R and R1 are directly linked to one another so that they form a bicyclic structural element together with the phenylenediamine partial structure, and R2, R3, R4 and R5 independently of one another denote hydrogen or an optionally substituted or heteroatom-comprising, saturated or unsaturated alkyl, cycloalkyl, aralkyl or aryl residue in ortho, meta or para position, and wherein the content of the polycyclic aromatic polyamines (II) and (III) and/or higher homologs thereof in the starting mixtures is 0.001 to 5 wt.%, based on the total weight of MDA, the polycyclic aromatic polyamines (II) and (III) and higher homologs thereof.

7. The polyisocyanate mixtures according to claim 6, wherein R and R1 independently of one another denote hydrogen or methyl and/or the residues R2 to R5 denote hydrogen.

8. The polyisocyanate mixtures according to claim 6, wherein the residue $(H_2N)_2C_6HRR1$ in formula (II) or $(H_2N)_2 C_6RR1$ in formula (III) is derived from o-phenylenediamine, 1,2-diamino-3-methylbenzene or 1,2-diamino-4-methylbenzene.

9. The polyisocyanate mixtures according to claim 6, wherein the content of the polycyclic aromatic polyisocyanates that are derived from the said polycyclic aromatic polyamines (II) and (III) in the starting mixtures is 0.001 to 2 wt. %, based on the total weight of MDI and the polycyclic aromatic polyisocyanates that are derived from the polycyclic aromatic polyamines (II) and (III) and higher homologs thereof.

10. A method for the production of polyurethane materials comprising incorporating the polyisocyanate mixtures according to claim 5.

* * * * *